United States Patent
Miyamura et al.

(10) Patent No.: US 10,517,978 B2
(45) Date of Patent: Dec. 31, 2019

(54) DEODORANT COMPOSITION, DEODORANT FABRIC, AND FIBER PRODUCT

(71) Applicant: Suminoe Textile Co., Ltd., Osaka-shi, Osaka (JP)

(72) Inventors: Yoshinari Miyamura, Nara (JP); Yukinori Shimomura, Nara (JP)

(73) Assignee: Suminoe Textile Co., Ltd., Osaka-shi, Osaka (JP)

(*) Notice: Subject to any disclaimer, the term of this patent is extended or adjusted under 35 U.S.C. 154(b) by 0 days.

(21) Appl. No.: 15/559,952

(22) PCT Filed: Feb. 8, 2016

(86) PCT No.: PCT/JP2016/053628
§ 371 (c)(1),
(2) Date: Sep. 20, 2017

(87) PCT Pub. No.: WO2016/158013
PCT Pub. Date: Oct. 6, 2016

(65) Prior Publication Data
US 2018/0071423 A1    Mar. 15, 2018

(30) Foreign Application Priority Data

Mar. 31, 2015  (JP) .................. 2015-072763

(51) Int. Cl.
| | | |
|---|---|---|
| *B01J 20/10* | (2006.01) | |
| *A61L 9/014* | (2006.01) | |
| *C01B 33/20* | (2006.01) | |
| *D06M 11/79* | (2006.01) | |
| *D06M 13/244* | (2006.01) | |
| *A61L 9/012* | (2006.01) | |
| *B01J 20/28* | (2006.01) | |
| *D06M 11/83* | (2006.01) | |
| *D06M 13/256* | (2006.01) | |
| *D06M 13/288* | (2006.01) | |

(52) U.S. Cl.
CPC .............. *A61L 9/014* (2013.01); *A61L 9/012* (2013.01); *B01J 20/10* (2013.01); *B01J 20/28033* (2013.01); *B01J 20/28038* (2013.01); *C01B 33/20* (2013.01); *D06M 11/79* (2013.01); *D06M 11/83* (2013.01); *D06M 13/244* (2013.01); *D06M 13/256* (2013.01); *D06M 13/288* (2013.01); *A61L 2209/22* (2013.01)

(58) Field of Classification Search
None
See application file for complete search history.

(56) References Cited

U.S. PATENT DOCUMENTS

| | | | | |
|---|---|---|---|---|
| 2009/0263343 | A1* | 10/2009 | Miyashita | ............... A61L 9/014 424/76.1 |
| 2011/0123393 | A1* | 5/2011 | Kuhn | ..................... C07F 3/003 422/5 |

FOREIGN PATENT DOCUMENTS

| | | |
|---|---|---|
| CN | 1839099 A | 9/2006 |
| JP | 2005-087630 A | 4/2005 |
| JP | 2009-285164 A | 12/2009 |
| JP | 2013-158613 A | 8/2013 |
| JP | 2013158613 A * | 8/2013 |
| JP | 2014-008162 A | 1/2014 |
| JP | 2015-187317 A | 10/2015 |

OTHER PUBLICATIONS

International Search Report dated Mar. 1, 2016 issued in corresponding PCT/JP2016/053628 application (2 pages).
English Abstract of JP 2005-087630 A published Apr. 7, 2005.
English Abstract of JP 2009-285164 A published Dec. 10, 2009.
English Abstract of JP 2013-158613 A published Aug. 19, 2013.
English Abstract of JP 2014-008162 A published Jan. 20, 2014.
English Abstract of JP 2015-187317 A published Oct. 29, 2015.
Office Action in corresponding CN 201680020171.8 dated Sep. 27, 2019 (pp. 1-8).

* cited by examiner

*Primary Examiner* — Nannette Holloman
(74) *Attorney, Agent, or Firm* — Millen White Zelano and Branigan, PC; Csaba Henter

(57) ABSTRACT

A deodorant composition is capable of efficiently absorbing and removing sulfur-based gases, such as, methyl mercaptan and hydrogen sulfide. It also has excellent water dispersibility, and has excellent applicability to various fabrics, a deodorant fabric in which the deodorant composition is adhered to at least a part of a fabric, and a fiber product using the deodorant fabric at least in a part of a product. The deodorant composition contains a deodorant including a metal silicate and at least one type of an anionic surfactant selected from the group consisting of hydroxyethylidenephosphonic acid and a salt thereof, alkylsulfosuccinic acid and a salt thereof, alkylsulfonic acid and a salt thereof, and monoalkyl phosphate. The deodorant fabric is provided in which the deodorant composition is adhered to a portion of a fabric by a binder resin, and a fiber product in which the deodorant fabric is used in at least one portion.

16 Claims, 1 Drawing Sheet

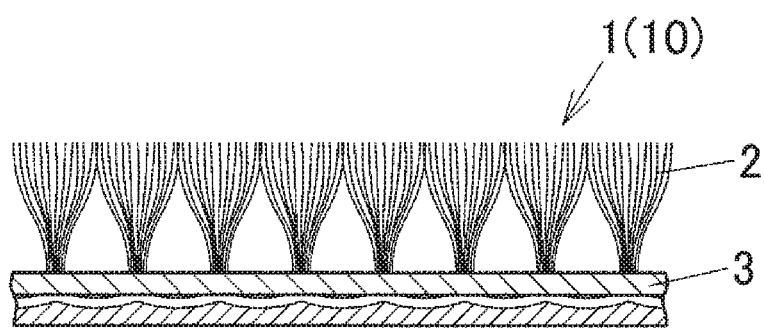

DEODORANT COMPOSITION, DEODORANT FABRIC, AND FIBER PRODUCT

TECHNICAL FIELD

The present invention relates to a deodorant composition capable of efficiently absorbing and removing sulfur-based gases, such as, e.g., mercaptans, particularly among unpleasant odors in the air in a room or unpleasant odors that adhere to familiar fiber products. It also relates to a deodorant fabric in which the deodorant composition is adhered to at least a portion of a fabric, and a fiber product using the deodorant fabric in at least a portion of a fabric. Such fiber products can be exemplified by, for example, nursing or nursing care products, medical care or sanitary products, bedding, shoes supplies, sporting goods, curtains, carpets, upholstery, non-woven fabrics, woven fabric wallpapers, etc. More specifically, the present invention relates to, for example, fiber products, such as, e.g., nursing or care clothing, underwear, bandages, gauze, masks, pouch covers, diapers, toilet deodorant sheets, toilet deodorant mats, trash can deodorant sheets, shoebox deodorant sheets, socks, shoe interior materials, insoles, bedding, shoes bags, and sportswear.

TECHNICAL BACKGROUND

For modern people, the problem of living odors is becoming a major concern. Further, the demand for deodorizing various unpleasant smells not only in houses but also in automobiles or indoor spaces of trains, airliners, etc., is increasing, and therefore methods for deodorizing unpleasant smells using deodorant compositions effective for various bad smells are disclosed. Furthermore, with the growing of interests in bad smells, demands for deodorizing bad smells in nursing or nursing care fields with the progress of aging society as well as unpleasant smells of familiar items, such as, e.g., clothing, bedding, and socks, and especially demands for deodorizing sulfur-based gases, such as mercaptans, is increasing.

Under the circumstances, the present applicant disclosed a technology related to deodorant compositions in which liquid stability is improved by blending an anionic surfactant and a nonionic surfactant in a deodorant composition including an amine compound, an inorganic porous material, a metal oxide, and a metal hydroxide (Patent Document 1).

PRIOR ART DOCUMENTS

Patent Documents

Patent Document 1: Japanese Unexamined Patent Application Publication No. 2009-285164

SUMMARY OF THE INVENTION

Problems to be Solved by the Invention

Generally, in order to impart deodorizing performance to fiber products such as fabrics, in many cases, a deodorant is dispersed in water and then applies to a fiber product. However, in cases where a metal silicate is used as a deodorant, when a surfactant having a chelate effect is combined, there occurs a problem that the metal becomes more likely to elute in water since the surfactant coordinates around the metal salt in the metal silicate. There also occurs a problem that the deodorizing performance deteriorates since the surfactant coordinates around the metal salt in the metal silicate. In addition, since the metal becomes more likely to elute in a solvent such as water, the washing durability is also poor, and therefore it is not practical.

The present invention was made in view of the aforementioned technical background, and aims to provide a deodorant composition capable of efficiently absorbing and removing sulfur-based gases, such as, e.g., methyl mercaptan and hydrogen sulfide, having excellent water dispersibility, and having excellent applicability to various fabrics, a deodorant fabric in which the deodorant composition is adhered to at least a part of a fabric, and a fiber product using the deodorant fabric in at least a part of a product.

Means to Solve the Problems

In order to achieve the aforementioned purpose, the present invention provides the following means.

[1] A deodorant composition comprising:
a deodorant including a metal silicate; and
at least one type of an anionic surfactant selected from the group consisting of hydroxyethylidenephosphonic acid and a salt thereof, alkylsulfosuccinic acid and a salt thereof, alkylsulfonic acid and a salt thereof, and monoalkyl phosphate.

[2] The deodorant composition as recited in the aforementioned Item [1], wherein the metal silicate is a copper silicate.

[3] The deodorant composition as recited in the aforementioned Item [1],
wherein a metal constituting the metal silicate includes:
copper, and
one, or two or more types of metals selected from the group consisting of zinc, manganese, cobalt, and nickel.

[4] A deodorant fabric in which the deodorant composition as recited in any one of the aforementioned Items [1] to [3] is adhered to at least a part of a fabric by a binder resin.

[5] A fiber product provided with the deodorant fabric as recited in the aforementioned Item [4] in at least a part of a product.

[6] A method of producing a deodorant fabric, comprising:
applying a processing solution comprising the deodorant composition as recited in any one of the aforementioned Items [1] to [3], water, and a binder resin to at least a part of a fabric.

Effects of the Invention

According to the invention recited in the aforementioned Item [1], since it includes a deodorant including a metal silicate and at least one type of an anionic surfactant selected from the group consisting of hydroxyethylidenephosphonic acid and a salt thereof, alkylsulfosuccinic acid and a salt thereof, alkylsulfonic acid and a salt thereof, and monoalkyl phosphate, it is possible to efficiently absorb and remove a sulfur-based gas, such as, e.g., methyl mercaptan and hydrogen sulfide. Moreover, since an anionic surfactant is blended, the water dispersibility is excellent, the deterioration of deodorizing performance can be suppressed, and further the applicability to various fabrics is excellent. In particular, even when the deodorant composition is adhered to a fiber fabric, the deodorizing performance can be demonstrated without causing problems in the friction fastness and texture of the fiber fabric.

According to the inventions recited in the aforementioned Items [2] and [3], since a sulfur-based gas, such as, e.g., methyl mercaptan and hydrogen sulfide, is effectively absorbed and removed, excellent deodorizing performance can be exhibited.

According to the invention recited in the aforementioned Item [4], since the deodorant composition is adhered to at least a part of a fabric by the binder resin, it is possible to provide a deodorant fabric having excellent washing resistance and abrasion resistance and capable of exhibiting a deodorant effect of efficiently absorbing and removing bad odor components of a sulfur-based gas, such as, e.g., mercaptan, for a long period of time.

According to the invention recited in the aforementioned Item [5], since the deodorant fabric is used for at least a part of the fiber product, the fiber product is capable of exhibiting a deodorant effect of efficiently absorbing and removing bad odor components of the fiber product and therearound, especially bad odor components of sulfur-based gases, such as, e.g., methyl mercaptan and hydrogen sulfide.

According to the invention recited in the aforementioned Item [6], it is possible to produce a deodorant fabric capable of efficiently absorbing and removing sulfur-based gases, such as, e.g., methyl mercaptan and hydrogen sulfide, exerting excellent washing resistance and abrasion resistance, and exerting a deodorant effect of efficiently absorbing and removing odor components of sulfur-based gases, such as, e.g., methyl mercaptan and hydrogen sulfide, for a long period of time.

BRIEF DESCRIPTION OF THE DRAWINGS

FIG. 1 is a cross-sectional view showing a carpet as one example of a fiber product constituted using a deodorant fabric according to the present invention.

EMBODIMENTS FOR CARRYING OUT THE INVENTION

In the present invention, since the metal silicate (a complex of a metal salt and a silicate) constituting the deodorant composition is powder and insoluble in water, the metal silicate is made to adhere to various fabrics as a deodorant composition uniformly dispersed in a solvent such as water. At that time, it was found that a deodorant containing a metal silicate (a complex of a metal salt and a silicate) and a deodorant composition containing a specific anionic surfactant are excellent in water dispersibility, deterioration of the deodorizing performance can be suppressed, the liquid stability of the deodorant composition can be improved, and the applicability to various fabrics is excellent, and the present invention has been completed. As a silicate of the complex of a metal salt and a silicate, a sodium silicate, a potassium silicate, etc., can be exemplified.

In the present invention, it is preferable that the aforementioned metal silicate include a copper silicate. Alternatively, it is preferable that the metal constituting the metal silicate have a configuration including:

copper, and one or two or more metals selected from the group consisting of zinc, manganese, cobalt, and nickel.

In the present invention, as an anionic surfactant, one or two or more anionic surfactants selected from the group consisting of hydroxyethylidenephosphonic acid and a salt thereof, alkylsulfosuccinic acid and a salt thereof, alkylsulfonic acid and a salt thereof, and monoalkyl phosphate can be exemplified. The anionic surfactant adsorbs the dispersed particles and gives a negative charge to stabilize the solution by a repulsive force between negative charges.

It is preferable that the amount of the aforementioned anionic surfactant be 0.1 parts by mass to 5 parts by mass with respect to 100 parts by mass of a metal silicate. It is not preferable if it is less than 0.1 parts by mass since there is no effect on the stability of the dispersion liquid. It is also not preferable even if it exceeds 5 parts by mass since there is no great improvement in the stability of dispersion liquid that corresponds to the input amount and the viscosity of the deodorant composition increases.

The application amount of the deodorant composition to a fabric depends on the size of the indoor space to be deodorized, but is preferably 0.1 $g/m^2$ to 5 $g/m^2$ (dry weight). It is not preferable when it is less than 0.1 $g/m^2$ since sufficient removal performance cannot be obtained. Further, it is also not preferable when it exceeds 5 $g/m^2$ since there is no great improvement in the deodorizing performance and the cost increases uselessly. It is more preferably that the application amount be 0.5 $g/m^2$ to 3 $g/m^2$ (dry weight).

In a method of preparing a processing solution of the deodorant composition, initially, a processing solution consisting of a water dispersing liquid obtained by dispersing the deodorant composition and a binder resin in water is mixed. At this time, it is preferable to disperse the deodorant composition and the binder resin as much as possible, and it is more preferable that the binder resin form an emulsion state with water. In addition, when mixing, it is preferable to disperse the deodorant composition in water in advance and then disperse the binder resin since the deodorant composition and the binder resin can be more uniformly dispersed.

For the binder resin, any resin can be used. For example, a self-crosslinking acrylic resin, a methacrylic resin, a urethane resin, a silicone resin, a glyoxal resin, a vinyl acetate resin, a vinylidene chloride resin, a butadiene resin, a melamine resin, an epoxy resin, an acrylic-silicone copolymer resin, ethylene-vinylacetate copolymer resin, isobutylene-maleic anhydride copolymer resin, an ethylene-styrene-acrylate-methacrylate copolymer resin, etc., can be exemplified. Further, two or more of these resins may be mixed to form the binder resin.

To the processing solution of the deodorant composition, various additives, such as, e.g., a dispersant and a thickener, may be added for the purpose of improving various properties. The deodorant composition is adhered to a fabric by applying the processing solution obtained as described above to the fabric. The application method is not particularly limited, but, for example, a spraying method, an immersion method, a coating method, etc., can be exemplified. Further, it may be configured such that the deodorant composition is made to adhere by a spraying method or an immersion method after the fabric is cut and sewed into a shape of a product and then dried.

As described above, the processing solution is dried after the application. However, as the drying means, a heat treatment method is preferably adopted in view of the drying efficiency and the fact that the binder resin can be cured. It is preferable that the heat treatment temperature be 100 to 180° C. With the heat treatment at this temperature, the adhesiveness of the deodorant composition can be further enhanced, and the persistence and durability of the deodorizing performance can be further improved.

In the present invention, fibers constituting a fabric are not particularly limited, and fibers, such as, e.g., a polyester fiber, a polyamide fiber, a polypropylene fiber, an acrylic fiber, and a rayon fiber, can be suitably used. Other natural fibers, such as, e.g., hemp, cotton, and wool, can also be used.

The form of the deodorant fabric 1 according to the present invention is not particularly limited, and a woven fabric, a knitted fabric, a non-woven fabric, a napped fabric, such as, e.g., a tufted carpet and a moquette (see FIG. 1), can be exemplified. FIG. 1 shows a carpet as one example of a fiber product 10 constituted using the deodorant fabric 1 according to the present invention. In this deodorant fabric 1, the deodorant composition may be applied to the pile 2, to the base fabric 3, or to both the pile 2 and the base fabric 3, or it may be applied to the entirety (entire portion) of the fabric.

The fiber product 10 of the present invention is not particularly limited as long as it is a fiber product using the deodorant fabric 1 in at least a part of the product, but may be exemplified by nursing or nursing care products, medical care or sanitary products, bedding, shoes supplies, sporting goods, curtains, carpets, upholstery, non-woven fabrics, woven fabric wallpapers, etc., since the fiber product 10 can efficiently absorb sulfur-based gases, such as, e.g., mercaptans, among unpleasant smells adhered to familiar fiber products. More specifically, the more preferable fiber product 10 is, for example, nursing or care clothing, underwear, bandages, gauze, masks, pouch covers, diapers, toilet deodorant sheets, toilet deodorant mats, trash can deodorant sheets, shoebox deodorant sheets, socks, shoe interior materials, insoles, bedding, shoes bags, sportswear, etc.

EXAMPLES

Next, specific examples of the present invention will be described, but it should be noted that the present invention is not particularly limited to these examples.

Example 1

After adding 20 parts by mass of a copper silicate, 2 parts by mass of hydroxyethylidenephosphonic acid, and 78 parts by mass of water, it was stirred by a mixer to obtain a deodorant composition. Further, 5 parts by mass of an acrylic binder resin (solid content: 50%) and 85 parts by mass of water were added to 10 parts by mass of the deodorant composition and stirred by the mixer to obtain a processing solution. A polyester fabric (weight per unit area 150 g/m$^2$) was immersed in the processing solution, squeezed with a mangle (amount of pick up: 100 g/m$^2$), and then dried at 130° C. for 15 minutes to obtain a deodorant fabric. The adhesion amount to the deodorant fabric was 2 g/m$^2$ of the copper silicate, 0.2 g/m$^2$ of the hydroxyethylidenephosphonic acid, and 2.5 g/m$^2$ of the acrylic binder resin.

TABLE 1

| | Compound composition of deodorant composition | | | |
| --- | --- | --- | --- | --- |
| | Metal silicate (type/parts by mass) | Anionic surfactant (type/parts by mass) | water (parts by mass) | Liquid stability Evaluation |
| Ex. 1 | Copper silicate/20 parts by mass | hydroxyethylidenephosphonic acid/2 parts by mass | 78 parts by mass | ○ |
| Ex. 2 | Silicate of copper and zinc/20 parts by mass | hydroxyethylidenephosphonic acid/2 parts by mass | 78 parts by mass | ○ |
| Ex. 3 | Silicate of copper and manganese/20 parts by mass | hydroxyethylidenephosphonic acid/2 parts by mass | 78 parts by mass | ○ |
| Ex. 4 | Copper silicate/20 parts by mass | hydroxyethylidenephosphonic acid/0.2 parts by mass | 79.8 parts by mass | ○ |
| Ex. 5 | Copper silicate/20 parts by mass | hydroxyethylidenephosphonic acid/4 parts by mass | 76 parts by mass | ○ |
| Ex. 6 | Copper silicate/20 parts by mass | alkylsulfosuccinic acid/2 parts by mass | 78 parts by mass | ○ |
| Ex. 7 | Copper silicate/20 parts by mass | alkylsulfonic acid/2 parts by mass | 78 parts by mass | ○ |
| Ex. 8 | Copper silicate/20 parts by mass | monoalkyl phosphates/2 parts by mass | 78 parts by mass | ○ |
| Comp. Ex. 1 | — | hydroxyethylidenephosphonic acid/2 parts by mass | 98 parts by mass | X |
| Comp. Ex. 2 | Copper silicate/20 parts by mass | — | 80 parts by mass | X |
| Comp. Ex. 3 | Copper silicate/20 parts by mass | Sodium polyacrylate/2 parts by mass | 78 parts by mass | X |
| Comp. Ex. 4 | Copper silicate/20 parts by mass | Polyoxyalkylene alkyl ether/2 parts by mass | 78 parts by mass | X |

Examples 2 to 8, Comparative Examples 1 to 4

A deodorant composition and a deodorant fabric were obtained in the same manner as in Example 1 except that the compound composition of the deodorant composition was set as shown in Table 1. Also, the evaluation results of the liquid stability are listed in Table 1. Further, the composition of the processing solution to be adhered to the fabric is shown in Table 2, the adhesion amount to the fabric is shown in Table 3, the odorous component reduction rate and the evaluation when the deodorization test using methyl mercaptan and hydrogen sulfide were performed respectively.

TABLE 2

| | Composition of processing solution | | | |
|---|---|---|---|---|
| | Metal silicate (type/parts by mass) | Anionic surfactant (type/parts by mass) | Binder resin (type/parts by mass) | Water (parts by mass) |
| Ex. 1 | Copper silicate/2 parts by mass | hydroxyethylidenephosphonic acid/0.2 parts by mass | Acrylic resin/5 parts by mass | 92.8 parts by mass |
| Ex. 2 | Silicate of copper and zinc/2 parts by mass | hydroxyethylidenephosphonic acid/0.2 parts by mass | Acrylic resin/5 parts by mass | 92.8 parts by mass |
| Ex. 3 | Silicate of copper and manganese/2 parts by mass | hydroxyethylidenephosphonic acid/0.2 parts by mass | Acrylic resin/5 parts by mass | 92.8 parts by mass |
| Ex. 4 | Copper silicate/2 parts by mass | hydroxyethylidenephosphonic acid/0.02 parts by mass | Acrylic resin/5 parts by mass | 92.98 parts by mass |
| Ex. 5 | Copper silicate/2 parts by mass | hydroxyethylidenephosphonic acid/0.4 parts by mass | Acrylic resin/5 parts by mass | 92.6 parts by mass |
| Ex. 6 | Copper silicate/2 parts by mass | alkylsulfosuccinic acid/0.2 parts by mass | Acrylic resin/5 parts by mass | 92.8 parts by mass |
| Ex. 7 | Copper silicate/2 parts by mass | alkylsulfonic acid/0.2 parts by mass | Acrylic resin/5 parts by mass | 92.8 parts by mass |
| Ex. 8 | Copper silicate/2 parts by mass | monoalkyl phosphates/0.2 parts by mass | Acrylic resin/5 parts by mass | 92.8 parts by mass |
| Comp. Ex. 1 | — | hydroxyethylidenephosphonic acid/0.2 parts by mass | Acrylic resin/5 parts by mass | 94.8 parts by mass |
| Comp. Ex. 2 | Copper silicate/2 parts by mass | — | Acrylic resin/5 parts by mass | 93 parts by mass |
| Comp. Ex. 3 | Copper silicate/2 parts by mass | Sodium polyacrylate/0.2 parts by mass | Acrylic resin/5 parts by mass | 92.8 parts by mass |
| Comp. Ex. 4 | Copper silicate/2 parts by mass | Polyoxyalkylene alkyl ether/0.2 parts by mass | Acrylic resin/5 parts by mass | 92.8 parts by mass |

TABLE 3

| | Adhesion amount to fabric (g/m$^2$) | | |
|---|---|---|---|
| | Metal silicate | Anionic surfactant | Binder resin |
| Ex. 1 | 2 | 0.2 | 2.5 |
| Ex. 2 | 2 | 0.2 | 2.5 |
| Ex. 3 | 2 | 0.2 | 2.5 |
| Ex. 4 | 2 | 0.02 | 2.5 |
| Ex. 5 | 2 | 0.4 | 2.5 |
| Ex. 6 | 2 | 0.2 | 2.5 |
| Ex. 7 | 2 | 0.2 | 2.5 |
| Ex. 8 | 2 | 0.2 | 2.5 |
| Comp. Ex. 1 | — | 0.2 | 2.5 |
| Comp. Ex. 2 | 2 | — | 2.5 |
| Comp. Ex. 3 | 2 | 0.2 | 2.5 |
| Comp. Ex. 4 | 2 | 0.2 | 2.5 |

<Liquid Stability>

After leaving a compounding solution as described in Table 1 for 120 hours under an environment of 45° C., each of the compounding solutions was visually judged. When any of aggregation, sedimentation or elution of metal was not recognized, it was evaluated as "◯", and when any of them was recognized, it was evaluated as "x".

<Deodorant Test>

The measurement of the deodorant was performed according to SEK mark fiber product authentication standard (JEC 301, revised on Apr. 1, 2013, Japan Textile Evaluation Technology Council).

(Methyl Mercaptan Deodorizing Performance)

After placing a test sample (10 cm×10 cm) in a bag having an inner capacity of 5 L, 3 L of a methyl mercaptan gas was injected so that the concentration became 8 ppm in the bag, and the residual concentration of the methyl mercaptan gas was measured after 2 hours. Then, a blank was prepared in the same manner except that no test sample was added, the residual concentration of the methyl mercaptan gas of the blank was measured, and from both measured values, the total amount in which the methyl mercaptan gas was removed was calculated. From this, the odorous component reduction rate (%) of the methyl mercaptan gas was calculated.

(Hydrogen Sulfide Deodorizing Performance)

The odorous component reduction rate (%) of the hydrogen sulfide was calculated in the same manner as in the aforementioned methyl mercaptan deodorizing performance measurement except that a hydrogen sulfide gas was injected instead of methyl mercaptan so that the concentration became 4 ppm in the bag.

And those with an odorous component reduction rate of 90% or more were evaluated as "⊙", those with an odorous component reduction rates of 80% or more and less than 90% were evaluated as "◯", those with odorous component reduction rate were 70% or more and less than 80% were evaluated as "Δ", and those with an odorous component reduction rate of less than 70% were evaluated as "x".

<Washing Test>

A fabric subjected to 10 washings according to the washing method of SEK mark fiber product (JEC 326 revised on Apr. 1, 2014, Japan Textile Evaluation Technology Council) was evaluated by the deodorant test.

TABLE 4

| | Deodorant test results | | | | Deodorant test results (after 10 washings) | | | |
|---|---|---|---|---|---|---|---|---|
| | Methyl mercaptan Odor component reduction rate (%) | Evaluation | Hydrogen sulfide Odor component reduction rate (%) | Evaluation | Methyl mercaptan Odor component reduction rate (%) | Evaluation | Hydrogen sulfide Odor component reduction rate (%) | Evaluation |
| Ex. 1 | 100 | ◎ | 100 | ◎ | 86 | ○ | 96 | ◎ |
| Ex. 2 | 100 | ◎ | 100 | ◎ | 83 | ○ | 91 | ◎ |
| Ex. 3 | 100 | ◎ | 100 | ◎ | 82 | ○ | 88 | ○ |
| Ex. 4 | 100 | ◎ | 100 | ◎ | 80 | ○ | 84 | ○ |
| Ex. 5 | 100 | ◎ | 100 | ◎ | 88 | ○ | 96 | ◎ |
| Ex. 6 | 100 | ◎ | 100 | ◎ | 82 | ○ | 90 | ◎ |
| Ex. 7 | 100 | ◎ | 100 | ◎ | 83 | ○ | 94 | ◎ |
| Ex. 8 | 100 | ◎ | 100 | ◎ | 84 | ○ | 95 | ◎ |
| Comp. Ex. 1 | 0 | X | 0 | X | 0 | X | 0 | X |
| Comp. Ex. 2 | 92 | ◎ | 99 | ◎ | 78 | △ | 83 | ○ |
| Comp. Ex. 3 | 78 | △ | 82 | ○ | 56 | X | 64 | X |
| Comp. Ex. 4 | 75 | △ | 80 | ○ | 51 | X | 69 | X |

As it is apparent from Table 1, the deodorant composition of the present invention is excellent in liquid stability. Further, as it is apparent from Table 4, the deodorant fabric of the present invention is a fabric having excellent methyl mercaptan and hydrogen sulfide removal performance, and also exhibits excellent deodorizing performance even after repeated washing.

INDUSTRIAL APPLICABILITY

Since the deodorant composition of the present invention is capable of efficiently absorbing and removing sulfur-based gases, such as, e.g., methyl mercaptan and hydrogen sulfide, and has excellent water dispersibility, it is suitably used to give deodorizing performance to fabrics used in nursing and nursing care facilities, etc., as well as in homes. Furthermore, the deodorant fabric of the present invention can be suitably applied to at least a portion of fiber products, such as, e.g., nursing or nursing care products, medical or sanitary products, bedding, shoes supplies, sporting goods, curtains, carpets, upholstery, non-woven fabrics, and woven fabric wallpapers.

This application claims priority claim of Japanese Patent Application No. 2015-72763 filed on Mar. 31, 2015, the entire disclosure of which is incorporated herein by reference in its entirety.

The terms and descriptions used herein are used only to describe the embodiments according to the present invention, and the present invention is not limited to them. The present invention allows any design-changes falling within the claimed scope of the present invention unless it deviates from the spirits of the invention.

DESCRIPTION OF SYMBOLS

1: deodorant fabric
10: fiber product

The invention claimed is:

1. A deodorant composition comprising:
a metal silicate; and
at least one anionic surfactant, which is hydroxyethylidenephosphonic acid or a salt thereof, or monoalkyl phosphate.

2. The deodorant composition as recited in claim 1, wherein the metal silicate is a copper silicate.

3. The deodorant composition as recited in claim 1, wherein a metal in the metal silicate includes:
copper, and
one or more of zinc, manganese, cobalt, and nickel.

4. A deodorant fabric, comprising the deodorant composition as recited in claim 1, which is adhered to at least a part of a fabric by a binder resin.

5. A fiber product, comprising the deodorant fabric as recited in claim 4 in at least a part of said fiber product.

6. A method of producing a deodorant fabric, comprising: applying a processing solution comprising the deodorant composition as recited in claim 1, water, and a binder resin to at least a part of a fabric.

7. The deodorant composition as recited in claim 1, wherein the at least one anionic surfactant is hydroxyethylidenephosphonic acid.

8. The deodorant composition as recited in claim 1, wherein the at least one anionic surfactant is a salt of hydroxyethylidenephosphonic acid.

9. The deodorant composition as recited in claim 1, wherein the at least one anionic surfactant is monoalkyl phosphate.

10. A deodorant fabric, comprising the deodorant composition as recited in claim 7, which is adhered to at least a part of a fabric by a binder resin.

11. A deodorant fabric, comprising the deodorant composition as recited in claim 8, which is adhered to at least a part of a fabric by a binder resin.

12. A deodorant fabric, comprising the deodorant composition as recited in claim 9, which is adhered to at least a part of a fabric by a binder resin.

13. A method for deodorizing a smell, comprising contacting said smell with a deodorant composition as recited in claim 1.

14. A method for deodorizing a smell, comprising contacting said smell with a deodorant composition as recited in claim 7.

15. A method for deodorizing a smell, comprising contacting said smell with a deodorant composition as recited in claim 8.

16. A method for deodorizing a smell, comprising contacting said smell with a deodorant composition as recited in claim 9.

\* \* \* \* \*